(12) United States Patent
Purcell

(10) Patent No.: US 7,087,076 B2
(45) Date of Patent: Aug. 8, 2006

(54) REFLECTIVE HEAT PATCH

(75) Inventor: Ricky W. Purcell, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 109 days.

(21) Appl. No.: 10/646,384

(22) Filed: Aug. 21, 2003

(65) Prior Publication Data

US 2005/0043776 A1    Feb. 24, 2005

(51) Int. Cl.
*A61F 7/00* (2006.01)
(52) U.S. Cl. .......................................... 607/114; 607/96
(58) Field of Classification Search .................. 607/96, 607/112, 114; 126/263.01, 263.02, 204; 428/702
See application file for complete search history.

(56) References Cited

U.S. PATENT DOCUMENTS

| | | | | |
|---|---|---|---|---|
| 3,867,939 A * | 2/1975 | Moore et al. | ............... | 604/291 |
| 4,245,149 A * | 1/1981 | Fairlie | ........................ | 219/528 |
| 4,596,250 A * | 6/1986 | Beisang et al. | ............. | 607/114 |
| 4,925,743 A | 5/1990 | Ikeda et al. | .................. | 428/702 |
| 5,737,774 A | 4/1998 | Petty-Saphon et al. | .......... | 2/69 |
| 5,918,590 A * | 7/1999 | Burkett et al. | ......... | 126/263.02 |
| 6,294,758 B1 | 9/2001 | Masao et al. | ................ | 219/217 |
| 6,336,935 B1 * | 1/2002 | Davis et al. | ................ | 607/112 |
| 6,453,648 B1 * | 9/2002 | Zhang et al. | .................. | 53/469 |
| 6,465,708 B1 | 10/2002 | Augustine | ..................... | 602/42 |
| 6,580,012 B1 * | 6/2003 | Augustine et al. | ............ | 602/42 |
| 6,648,909 B1 * | 11/2003 | Helming | ..................... | 607/108 |
| 2002/0119186 A1 | 8/2002 | Zhang et al. | ............... | 424/449 |

FOREIGN PATENT DOCUMENTS

| | | |
|---|---|---|
| JP | 02174861 | 7/1990 |
| WO | WO-8600219 A1 | 1/1986 |
| WO | WO-9736027 | 10/1997 |
| WO | WO-9962302 A1 | 12/1999 |

* cited by examiner

*Primary Examiner*—Roy D. Gibson
(74) *Attorney, Agent, or Firm*—Schwegman, Lundberg, Woessner & Kluth, P.A.

(57) ABSTRACT

A heat patch and method for providing therapy to a body. The heat patch includes a reflective layer and a heat source that is attached to the reflective layer. The reflective layer reflects infrared energy emitted by the body back into the body while the heat source applies heat to the body. The combination of supplying heat and reflecting infrared energy provides effective therapy to people with relatively deep tissue injuries. In another aspect, the heat patch includes an enclosure made from a gas-permeable layer and a reflective layer attached to the gas-permeable layer. A heating composition is sealed inside the enclosure to generate heat when a gas (e.g., air) is received through the gas-permeable layer. The heat generated by the heating composition is easily controlled such that heat patch can be maintained at a temperature well above ambient temperature.

6 Claims, 2 Drawing Sheets

REFLECTIVE HEAT PATCH

FIELD

The present invention relates to a heat patch and more particularly to a heat patch that transfers heat to a body and reflects infrared energy into the body when the heat patch is placed on or near the body.

BACKGROUND

A variety of heat-treating methods are used to treat symptoms such as stiffness, muscle pain, cold hands and feet, lumbago, rheumatism and neuralgia (among others). Some known heat-treating methods include direct application of heat to the body using items such as a towel, jelly and/or paste. One concern with such heat-treating methods relates to their ability to apply heat for extended periods of time.

Another heat-treating method utilizes a heat patch to apply heat to an injured portion of a body. Many heat patches generate heat internally, such as via an exothermic chemical reaction, to raise the temperature of the heat patch. The temperature of the heat patch must be limited because applying too much heat to the body causes discomfort or burning. The level of heat that may be safely applied by heat patches is typically insufficient to provide adequate therapy to deeper muscles or joints within the body.

Another treatment method places a reflector on a body to reflect the infrared energy which is emitted from the body back into the body. Infrared energy penetrates deeply into the tissues of the body to provide physiological benefits that are believed to promote patient healing and increase patient comfort. One concern with using reflectors is that they typically do not reflect enough infrared energy to provide optimal therapy, especially when the ambient temperature near the body is low.

Accordingly, there is a need for a heat patch that is capable of providing therapy to deeper areas of the body without burning the skin surface. The heat patch should also be able to apply heat to an injured area of the body for extended periods of time. There is also a need for a heat patch that can be regulated at a temperature which is significantly greater than typical ambient temperature.

SUMMARY OF THE INVENTION

The present invention relates to a heat patch that generates heat and reflects infrared energy. The heat supplied by the heat patch is sufficient to maintain the temperature of the heat patch well above typical ambient temperatures. As the body is warmed by the heat patch, the body generates more infrared energy which is then reflected back into the body by the heat patch. The infrared energy that passes from the body is inherently efficient at passing through tissue. Therefore, when such infrared energy is reflected back into the tissue it is similarly effective at passing through tissue to deeply penetrate the body.

In one aspect, the present invention relates to a heat patch for providing therapy to a body. The heat patch includes a reflective layer and a heat source that is attached to the reflective layer. The reflective layer reflects infrared energy emitted by the body back into the body while the heat source applies heat to the body. The combination of supplying heat and reflecting infrared energy potentially provides superior therapy to people with relatively deep tissue injuries.

In another aspect, the present invention relates to a heat patch for providing therapy to a body where the heat patch includes an enclosure made from a gas-permeable layer and a reflective layer that is attached to the gas-permeable layer. A heating composition is sealed inside the enclosure. The heating composition generates heat when a gas (e.g., air) is received through the gas-permeable layer. The reflective layer reflects infrared energy emitted by the body back into the body. The heat generated by the heating composition is easily controlled such that heat patch can be maintained at a temperature that is well above ambient temperature.

In yet another aspect, the present invention relates to method of providing therapy to a body. The method includes applying heat to a portion of the body and reflecting infrared energy emitted by the body back into the portion of the body.

In an alternative aspect, the method of providing therapy to a body includes enabling an exothermic reaction within a heat patch to generate heat where the heat patch includes an enclosure formed of a gas-permeable layer and a reflective layer. The method further includes applying the heat patch to a portion of the body and reflecting infrared energy emitted by the body back into the portion of the body using the reflective layer on the heat patch. In some sample forms of the method, enabling an exothermic reaction within the heat patch may include exposing the heat patch to air to generate heat that maintains the temperature of the heat patch in a range of about 38 degrees centigrade to about 44 degrees centigrade.

The purposes and features of the present invention will be set forth in the description that follows. Additional features of the invention will be realized and attained by the product and processes particularly pointed out in the written description and claims hereof, as well as from the appended drawings.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the invention.

BRIEF DESCRIPTION OF THE DRAWINGS

The present invention will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

DETAILED DESCRIPTION OF THE INVENTION

In the following detailed description, reference is made to the accompanying drawings, which show specific embodiments in which the invention may be practiced. These embodiments are described in sufficient detail to enable those skilled in the art to practice the invention. It is to be understood that other embodiments may be utilized and structural changes made, such that the following detailed description is not to be taken in a limiting sense.

Figure 1:
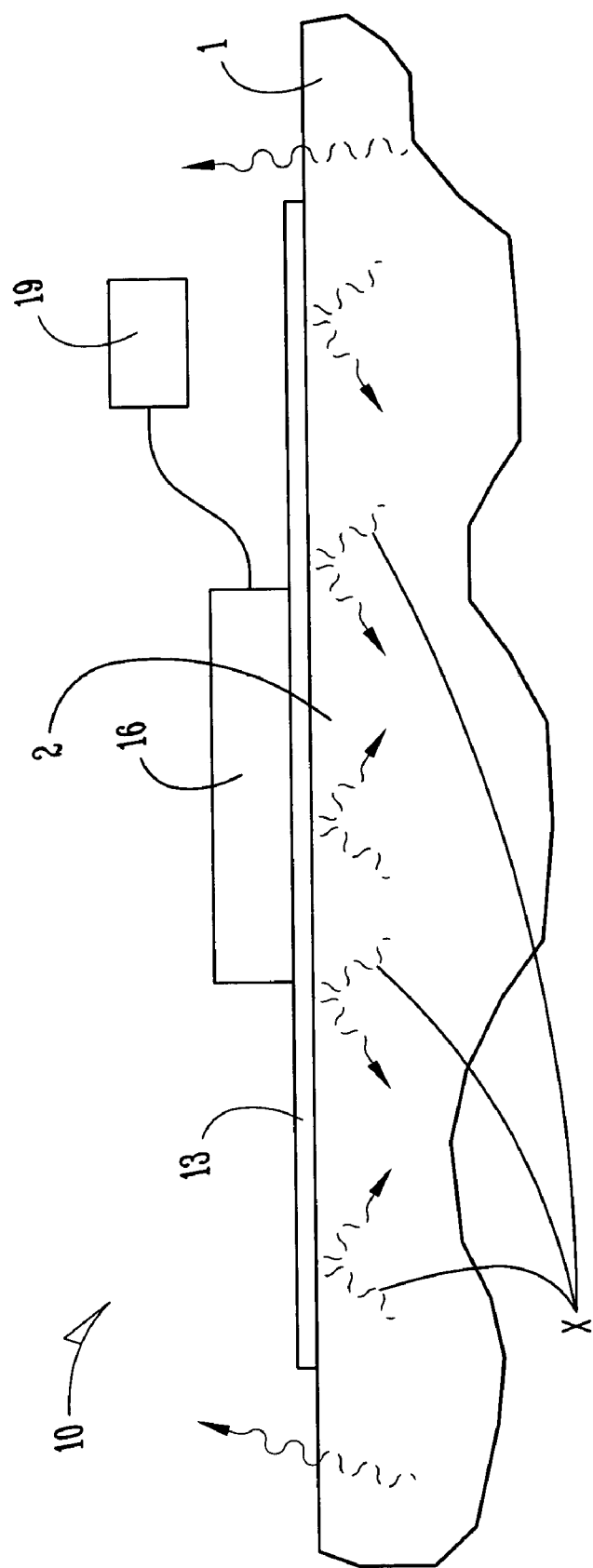
FIG. 1 illustrates a schematic section view of the heat patch.

FIG. 1 illustrates a heat patch 10 for providing therapy to a portion 2 of a body 1. The heat patch 10 includes a reflective layer 13 and a heat source 16 that is attached to the reflective layer 13. The reflective layer 13 reflects infrared energy X emitted by the body 1 back into the portion 2 of the body 1, and the heat source 16 applies heat to the body 1.

The combination of generated heat and reflected infrared energy provides effective therapy to the portion 2 of the body 1. The heat applied by the heat patch 10 not only applies therapy to the portion 2 of the body, but increases the amount of infrared energy emitted from the body 1. Since more infrared energy X is emitted from the body 1 when heat is applied to the body 1, then more infrared energy X is reflected back into the portion 2 of the body 1 by the reflective layer 13 to provide even more effective therapy to the body 1.

The reflective layer 13 may be aluminized polyester film (among other materials). The relative size and shape of the reflective layer 13 and the heat source 16 will depend on the size and shape of the portion 2 on the body 1.

Although any type of heat source 16 may be used in the heat patch 10, in some sample forms, heat source 16 may be a resistive element that generates heat when current is supplied to the resistive element by a power source (e.g., a battery). In addition, the heat patch 10 may further include a controller 19 (e.g., a computer system) that is connected to the heat source 16 to control the rate at which heat is supplied by the heat source 16.

Figure 2:
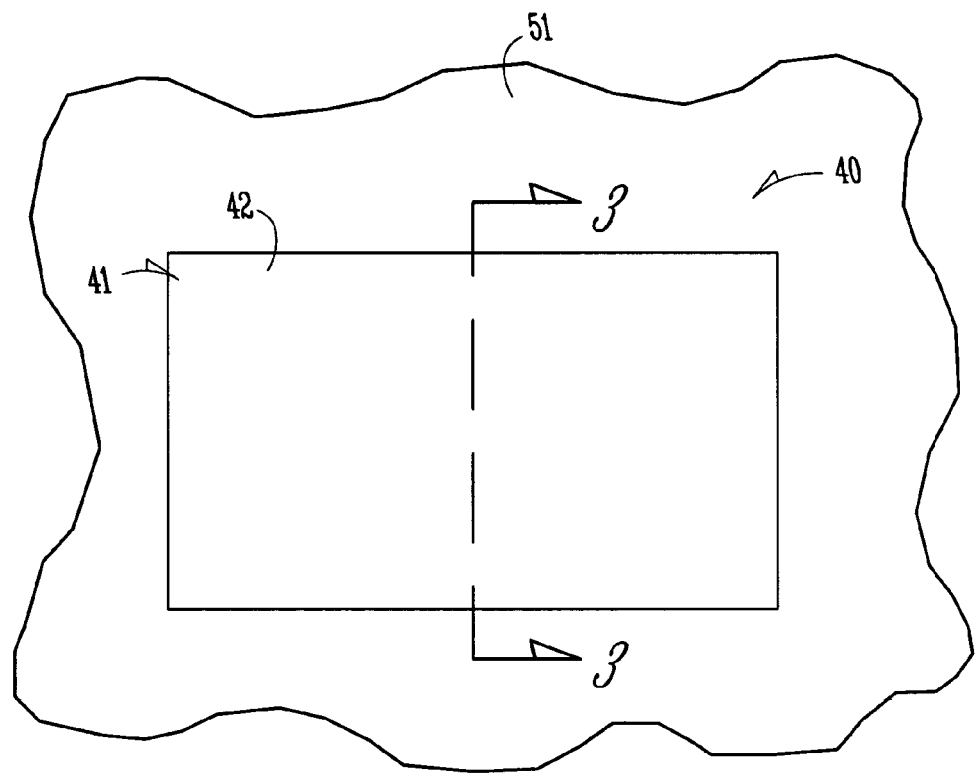
FIG. 2 illustrates a top view of another heat patch.
Figure 3:
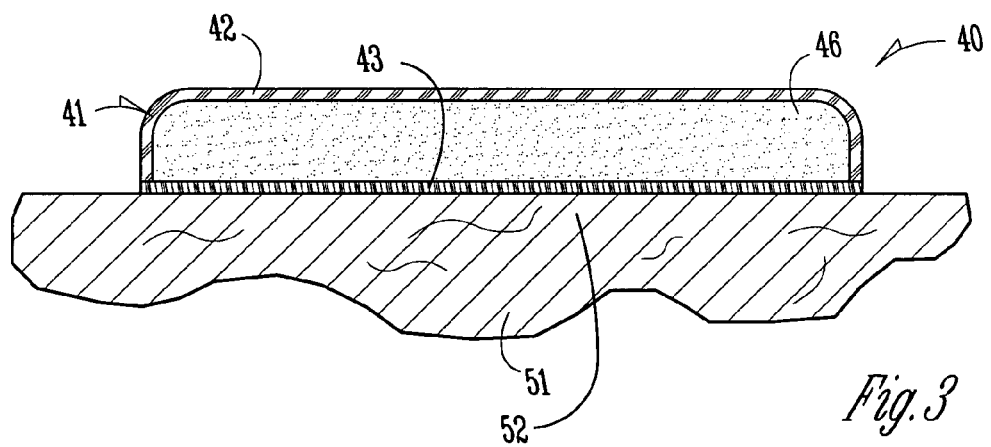
FIG. 3 illustrates a section view of the heat patch shown in FIG. 2 taken along line 3—3.

FIGS. 2 and 3 illustrate a heat patch 40. The heat patch 40 includes an enclosure 41 having a gas-permeable layer 42 and a reflective layer 43 that is attached to the gas-permeable layer 42. A heating composition 46 (see FIG. 3) is sealed inside the enclosure 41. The heating composition 46 is capable of generating heat when a gas, such as oxygen contained in ambient air, is received through the gas-permeable layer 42.

The reflective layer 43 of the enclosure 41 is positioned on, or near, the skin such that the heat patch 40 applies heat directly, or indirectly, to a portion 52 of the body 51. The reflective layer 43 is similar to the reflective layer 13 described above with regard to FIG. 1 in that reflective layer 43 also reflects infrared energy emitted from the body 51 back into the injured portion 52 of the body 51.

The heat patch 40 is stored in a hermetic environment (e.g., a sealed bag) such that the heating composition 46 remains inactivate until the heat patch 40 is removed from the hermetic environment. Heat patch 40 may be placed in the gas-tight sealed bag alone, or with additional heat patches that are part of a single piece which is folded for storage into the sealed bag. The individual patches could then be cut from the single piece before being applied on or near a body.

Once the heat patch 40 is removed from the hermetic environment and exposed to air, an exothermic reaction takes place. The exothermic reaction generates heat that raises the temperature of the heat patch 40. Increasing the rate at which the exothermic reaction takes place within the enclosure 41 causes the temperature of the heat patch 40 to rise, but reduces the duration of the exothermic reaction. The rate at which the exothermic reaction takes place is controlled by limiting the supply of air that feeds the exothermic reaction within the heat patch 40.

In some sample forms, a gas-impermeable cover (not shown) may be detachably mounted to the gas-permeable layer 42 to limit the supply of air that can pass through gas-permeable layer 42. Although the entire gas-permeable layer 42 is shown as being gas permeable, in some alternative forms, certain section(s) of the layer 42 will be gas-impermeable.

As long as the supply of air remains constant, the exothermic reaction within heat patch 40 maintains the temperature of the heat patch 40 at a predetermined level over a long period of time. As an example, heat patch 40 may be maintained at 38 degrees C. when some of gas-permeable layer 42 is sealed, and may be maintained at 44 degrees C. when the entire gas-permeable layer 42 is exposed. The temperature of the heat patch 40 and length of heating time depend on how much of the gas-permeable layer 42 is exposed at any one particular time.

The perimeter of the reflective layer 43 is bonded to the perimeter of the gas-permeable layer 42 by such means as adhesion, melt-bonding or sewing (among others). As an example, one edge of the joined gas-permeable layer 42 and reflective layer 43 may be left open, and after the heating composition 46 is inserted, the open edge is sealed to form the enclosure 41. It should be noted that any size, number and arrangement of layers may be utilized in forming the heat patch 40 as long it includes a gas-permeable layer and a reflective layer.

Another example may include fabricating the heat patch 40 using a layering approach in which a layer of heating composition 46 is deposited on the gas-permeable layer 42. The reflective layer 43 is then positioned on the heating composition 46 while the perimeter edges of the enclosure 41 are simultaneously sealed to entrap the heating composition 46.

The gas-permeable layer 42 may be polyethylene or polypropylene non-woven fabric (among other materials). Any conventional heating composition 46 may be used to induce an exothermic reaction in the presence of a gas such as air. Some example heating compositions 46 include any combination of iron powder, water, water-retaining agent, reaction promoter and salt.

In alternative forms, a release layer (not shown) may be detachably mounted to the reflective layer 43 using an adhesive. The release layer may be removed from the reflective layer 43 leaving only the adhesive on the reflective layer 43. The remaining adhesive provides a means for directly, or indirectly, securing the heat patch 40 to the body 51.

A method of providing therapy to a body 1 is described herein with reference to FIG. 1. The method includes applying heat to a portion 2 of the body 1 and reflecting infrared energy X emitted by the body 1 back into the portion 2 of the body 1.

In some sample forms of the method, applying heat to the portion 2 of the body 1 includes generating heat within a heat patch 10 and applying the heat patch 10 to the portion 2 of the body 1. Generating heat within the heat patch 10 may include delivering current through a resistive element or enabling an exothermic reaction within the heat patch 10 (among other ways to generate heat). In addition, generating heat within the heat patch 10 may include controlling the heat generated by the heat patch 10.

It should be noted that reflecting infrared energy may include reflecting infrared energy having wavelengths in a range of about 3 to 50 microns, especially having wavelengths near 10 microns. In addition, reflecting infrared energy may include positioning a reflective layer 13 on the heat patch 10 on, or near, the portion 2 of the body 1.

Another method of providing therapy to a body 51 is described herein with reference to FIGS. 2 and 3. In one form, the method includes enabling an exothermic reaction within a heat patch 40 to generate heat. The heat patch 40 includes an enclosure 41 that is formed of a gas-permeable layer 42 and a reflective layer 43. The method further includes attaching the heat patch 40 to a portion 52 of the body 51 and reflecting infrared energy X emitted by the body 51 back into the portion 52 of the body 51 using the reflective layer 43 on the heat patch 40. Enabling an exothermic reaction within the heat patch 40 may include exposing the heat patch 40 to air in order to maintain the heat patch 40 at a temperature in a range of about 38 degrees centigrade to about 44 degrees centigrade.

The operations discussed above with respect to the described methods may be performed in a different order from those described herein. It should be noted that attaching a heat patch to a body includes attaching the heat patch directly, or indirectly, to the body. In addition, FIGS. 1–3 are representational and are not necessarily drawn to scale. Certain proportions thereof may be exaggerated, while others may be minimized.

The heat patches and methods described herein allow a user or therapist to more easily control the temperature of a heat patch over a long period of time. The heat patches and methods are also effective in applying therapy to deep tissues within a human body.

While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

I claim:

1. A method of providing therapy to a body, the method comprising:
    applying a heat patch to a portion of the body such that a reflective layer on the heat patch directly engages the body;
    generating heat within the heat patch by delivering current through a resistive element; and
    reflecting infrared energy emitted by the body back into the portion of the body using the reflective layer on the heat patch.

2. The method of claim 1 wherein generating heat within the heat patch includes controlling the heat generated by the heat patch.

3. The method of claim 1 wherein reflecting infrared energy includes reflecting infrared energy having wavelengths in a range of about 3 to 50 microns.

4. A method of providing therapy to a body, the method comprising:
    enabling an exothermic reaction within a heat patch to generate heat, the heat patch including an enclosure formed of a gas-permeable layer and a reflective layer;
    applying the heat patch to a portion of the body such that the reflective layer directly engages the body; and
    reflecting infrared energy emitted by the body back into the portion of the body using the reflective layer on the heat patch.

5. The method of claim 4 wherein enabling an exothermic reaction within the heat patch includes exposing the heat patch to air.

6. The method of claim 4 wherein enabling an exothermic reaction within the heat patch to generate heat includes maintaining the heat patch at a temperature in a range of about 38 degrees centigrade to about 44 degrees centigrade.

* * * * *